US012805994B2

(12) United States Patent
Da Silva et al.

(10) Patent No.: US 12,805,994 B2
(45) Date of Patent: Nov. 24, 2026

(54) ANTIMICROBIAL DENTAL DEVICE FOR TISSUE REGENERATION, METHODS AND USES THEREOF

(71) Applicant: UNIVERSIDADE DO MINHO, Braga (PT)

(72) Inventors: Filipe Samuel Correia Pereira Da Silva, Braga (PT); Flávio Gabriel Silva Rodrigues, Fafe (PT); Sara Cristina Soares Madeira, Gerês (PT); João Pedro Figueiredo Pinto, Maia (PT)

(73) Assignee: UNIVERSIDADE DO MINHO, Braga (PT)

( * ) Notice: Subject to any disclaimer, the term of this patent is extended or adjusted under 35 U.S.C. 154(b) by 0 days.

(21) Appl. No.: 19/296,016

(22) Filed: Aug. 11, 2025

(65) Prior Publication Data

US 2026/0041537 A1 Feb. 12, 2026

(30) Foreign Application Priority Data

Aug. 9, 2024 (PT) ........................................ 119652

(51) Int. Cl.
*A61C 19/06* (2006.01)
*A61C 8/00* (2006.01)
*A61N 1/05* (2006.01)

(52) U.S. Cl.
CPC ............ *A61C 19/06* (2013.01); *A61C 8/0096* (2013.01); *A61N 1/0548* (2013.01)

(58) Field of Classification Search
None
See application file for complete search history.

(56) References Cited

U.S. PATENT DOCUMENTS 3,118,450 A * 1/1964 Freeman .............. A61C 19/063 433/25
3,215,139 A * 11/1965 Dietz ....................... A61K 8/02 433/32

(Continued)

FOREIGN PATENT DOCUMENTS

CN 110496306 A * 11/2019 ............. A61N 1/306
WO 2019082154 A1 5/2019

OTHER PUBLICATIONS

Bins-Ely et al. "Enhancing the bone healing on electrical stimuli through the dental implant." Comput Methods Biomech Biomed Engin. Nov. 2020;23(14):1041-1051. 29 pages.

(Continued)

*Primary Examiner* — Amy R Weisberg
(74) *Attorney, Agent, or Firm* — Leason Ellis LLP

(57) ABSTRACT

The present disclosure describes an antimicrobial dental device for tissue regeneration comprising:

a main body comprising an interior and an exterior surface;

electrodes to stimulate the tissue to regenerate and eliminate bacteria, connected by an electrical circuit; wherein the plurality of electrodes is impregnated throughout the interior of the main body for creating micro-electric fields;

a plurality of channels oriented from the outer surface towards the interior of the main body to receive a fluid and direct it to the electrical circuit for creating an electric flow;

an array of pillars which are hydrophilic, wherein the space between each pillar of the pillar array forms a network of capillary channels to receive and retain the electric flow from the plurality of channels near the tissue;

(Continued)

a hydrophobic and insulating zone inside the main body to repel the electric flow in a zone of the tissue to be protected.

19 Claims, 9 Drawing Sheets

(56) References Cited

U.S. PATENT DOCUMENTS

| | | | | |
|---|---|---|---|---|
| 3,259,129 | A * | 7/1966 | Tepper | A61F 5/58 607/58 |
| 5,433,725 | A | 7/1995 | Zanakis et al. | |
| 9,314,321 | B2 | 4/2016 | Nemeh et al. | |
| 11,484,708 | B2 | 11/2022 | Nagel et al. | |
| 2014/0093832 | A1* | 4/2014 | Nemeh | A61C 19/066 433/1 |
| 2016/0228228 | A1* | 8/2016 | Nemeh | A61N 1/205 |
| 2020/0281693 | A1* | 9/2020 | Correia Pereira Silva | A61C 13/0018 |
| 2020/0289242 | A1* | 9/2020 | Correia Pereira Silva | A61L 27/306 |
| 2023/0158283 | A1 | 5/2023 | Gao et al. | |

OTHER PUBLICATIONS

Bins-Ely et al. "In vivo electrical application on titanium implants stimulating bone formation." J Periodontal Res. Jun. 2017;52(3):479-484. 6 pages.

Gonçlves et al. "Electrical potential approaches to inhibit biofilm adhesion on titaniumimplants." Mater Lett. 2019; 255: 126577. 5 pages.

Rodrigues et al. "Zirconia Dental Implants Surface Electric Stimulation Impact on *Staphylococcus aureus*." Int J Mol Sci. May 24, 2024;25(11):5719. 17 pages.

* cited by examiner a)

b) c)

a) b) c)

a) b) c)

a) b)

a) b)

ANTIMICROBIAL DENTAL DEVICE FOR TISSUE REGENERATION, METHODS AND USES THEREOF

CROSS-REFERENCE TO RELATED APPLICATIONS

This application claims priority to Portugal Patent Application No. 119652, filed Aug. 9, 2024, the contents of which is hereby incorporated by reference in its respective entirety.

TECHNICAL FIELD

The present disclosure describes medical devices, more specifically antimicrobial dental devices intended for the regeneration of dental, bone and gingival tissues. Specifically, it concerns an antimicrobial mouthpiece device which, through electrical stimuli, promotes the elimination of bacteria and stimulates tissue regeneration, for example of gingiva, skin or bone, in the areas surrounding the device.

BACKGROUND

Tray-type mouthguards have various functions such as correcting the position of the teeth; protecting against tooth wear, for example in cases where individuals suffer from dysfunctions such as bruxism; correcting the position of the jaw; protecting the teeth against impacts in more aggressive sports such as boxing, rugby, etc.; or even assisting in the treatment of sleep apnea. In all the aforementioned cases, only the geometric shape of the trays is used to promote the stated functions.

However, there are some trays with additional functions, capable of accelerating orthodontic movement and bone regeneration processes. This is achieved through the use of light or vibration, with devices incorporated into the trays, or even through electric current generated by devices with dissimilar materials incorporated into the trays, resulting in voltaic cells.

The application of electrical stimuli on the surface of dental implants to promote bone regeneration and the elimination of bacteria has been validated in the state of the art through in vitro tests [1-3]. As for the use of electrical stimuli in tray-type mouthguards or dental bridges, there are no solutions that allow for localized control of electric currents, ensuring controlled and adequate current flows, both in terms of specific areas of action and current intensity.

Document U.S. Pat. No. 11,484,708 B2 proposes a solution for creating electric fields by incorporating materials that create voltaic cells between two dissimilar materials, for example silver and zinc, into medical devices and small reservoirs with different geometric shapes, thereby generating electric current flows between these materials, using an electrically conductive fluid that exists between the materials. This solution allows the creation of small and multiple electric fields along the surface of the devices. These electric fields are predetermined and cannot be altered, as they depend on the materials incorporated, their quantity, and geometry.

Document US2023/0158283 A1 presents a wound healing dressing with electrical stimuli, which provides solutions for creating electric fields that aid in healing. However, the document provides electrostimulation solutions, essentially between two poles, with designs specifically intended for wounds, but does not provide a homogeneous field of micro-electrical stimuli, and is also based on the creation of electric fields that do not generate electric currents in the liquid medium. On the other hand, they do not guarantee a constant liquid medium in the area where the micro-electric flows are intended. In US2023/0158283 A1, electric fields are created, but electric flows are not, as there is no direct contact between the electric poles and the fluid.

In the first case, US 2014/0093832 A1, where electric flows are created, these are highly random because, as the poles are distant, the electric current flow will flow through the area that is most favorable to the passage of electric current, i.e., that has the least resistance to the passage of electric current, and only through this area. As such, its action is very limited to this area and will therefore be poorly controlled. The action of the electric current flow will therefore be potentially effective only in the areas through which the electric current flows and less effective or ineffective in the areas where it does not flow. In addition, the electric current flow may be excessive and harmful to biological tissues if it is concentrated in a small volume of fluid in a particular favorable area, or it may be of low effectiveness if the current flow is spread over a larger volume. For example, assuming that the voltage poles are in the gingival area, if there is a gap between two teeth, the electric current flow will flow through the gap area between the teeth, as it is shortest path, and will not flow along the teeth surfaces, through a longer path of the tooth surface. In this case, as the current flow will be confined to a small area/volume, the electric current density will be high. If the teeth are touching and there is no space between them, the current will flow along the larger surface of the tooth, spreading over a much larger area/volume and causing a lower electric current density. Thus, the current flow and its density are highly random and poorly controllable. On the other hand, contact between the device and the tooth, gum, or skin is very irregular, and the presence of a uniform volume of liquid or gel that would allow for a controlled electric current flow is not guaranteed. In certain areas, there may be no conductive medium at all, while in others there may be, which causes substantial variations in the electric current flows. Since biological tissues (gums, bone, among others) and some biological entities such as bacteria are very sensitive to electric current density, and each responds differently to a specific electric flow, it is important that both electric current flows and their density be tightly controlled, locally, in order to be effective and thus achieve their purposes. Furthermore, as devices in the mouth simultaneously deal with cells, which need to be stimulated, and bacteria, some of which must be eliminated, it is important to act upon each biological entity with different energy densities in a controlled manner, according to the needs and purposes to be achieved in each area or biological entity.

Document US 2014/0093832 A1 proposes a solution consisting of mounting on the device, for example a tray, on its outer edges, two electrical wires, one with a positive charge and the other with a negative charge, powered by an external power source, which are intended to create the voltage poles between which the electric current flows are to be generated, which will pass from one pole to the other. Along the wire, there may be electrically insulated zones and some points that allow current to pass through. However, this solution leads to the creation of a single electric (and magnetic) field between two poles, or between several points, all located on the outer edges of the tray, in areas far away from the main body of the device and, therefore, quite far from each other. In the case of document US 2014/0093832 A1, there are only two or more poles mounted at relatively distant points, usually at the extreme points of the device, between which a single electric field or a few electric fields are created, which generate one or a few electric current flows. These electric fields will generate electric current flows between the two poles, thereby causing bone stimulation and/or the elimination of bacteria in the zones where the current passes through.

These facts are described in order to illustrate the technical problem solved by the embodiments of the present document.

GENERAL DESCRIPTION

The present disclosure relates to a dental device, preferably a mouthguard, whether a tray, dental bridge or healing dressing, which, in addition to its mechanical action, controls and/or eliminates bacteria present in the region (skin, teeth, implant surfaces, dental bridges, among others), also promotes bone and soft tissue regeneration, namely of the gums or other intraoral tissues and skin, in a controlled and thus highly effective manner. The device described in the present disclosure surprisingly contributes to preventing and reversing gingival recession or bone loss and to healing wounds such as canker sores, ulcers, or others.

In an embodiment, the device described in the present disclosure may be U-shaped and configured to be arranged over a plurality of a user's teeth, such as a tray-type mouthguard, or a dental bridge, or a healing dressing, which has the ability to interact with microorganisms present in the mouth, in particular on the teeth, gums or around dental implants, and consequently stimulate the elimination of bacteria and the regeneration of certain biological tissues such as gums, bone, skin or other intraoral tissues in the areas surrounding the device. In this way, it is possible to prevent bone or gum recession around the dental device, as well as stimulate bone regeneration during orthodontic movement around the device, in humans and animals.

The proposed device allows the generation of multiple customized micro-electric fields and micro-electric flows to prevent bone loss, stimulate bone, gum, and skin regeneration, and eliminate bacteria.

This device with micro-electrical stimuli allows the creation of multiple micro-electric fields that generate micro-electric flows and well-defined and controlled current densities, allocated at multiple points on the surface of the device.

The present disclosure also provides a hydrophilic surface texture that ensures the existence of a uniform electric conductive medium in the active zones through which the electric current is intended to flow, and a hydrophobic surface that inhibits electric current in the areas where electric current should not flow, thereby ensuring controlled conditions for the existence of perfectly controlled electric current densities, both in terms of current intensity and location thereof.

In an embodiment, the electrical system comprised in the dental device comprises a plurality of electrodes in a circuit of electrical wires with positive and negative poles, arranged alternately and distributed in parallel along the active area of the device. This electrical system is responsible for creating micro-electric fields at multiple points on the surface of the dental device.

In an embodiment, the device further comprises an electric field generator composed of a battery or a piezoelectric component and a patella.

In an embodiment, the electric field generator comprises a battery programmed to operate and create electric potentials along the electric circuit, either in value (Volts), or operating frequency (Hz), or even in the type of current, direct or alternating, or even in duration of action (seconds), located inside the mouthpiece device.

In an embodiment, the electric field generator is composed of a piezoelectric component, replacing the battery, disposed inside the device, assisted by a patella, which slides inside the piezoelectric component due to body movement, causing impacts against the walls of the piezoelectric component. These impacts will generate multiple micro-electric fields that will flow through the circuit of electrical wires inside the dental device described in this disclosure up to the surface thereof, wherein the value of the micro-electric fields may vary depending on the specific biological function.

The dental device, preferably the tray-type mouthpiece device, dental bridge or also healing dressing, has different regions with different types of surfaces, so as to ensure that, in the area where the micro-electric fields are to be created, it comprises a hydrophilic surface capable of retaining an electrically conductive fluid, such as a liquid, paste or gel medium, which will allow the creation of regulated electric current flows, and another hydrophobic and non-conductive surface that repels any fluid, liquid medium or gel, thereby allowing the containment of the micro-electric flows.

The state of the art relating to dental devices, particularly mouthguards or skin protectors, does not contemplate this type of solution for creating multiple micro-electrical stimuli, with micro-electric flows in biological tissues, along the body of the device, for mouthguards or healing dressings. Nor does it contemplate the creation of hydrophilic textures for electrically conductive areas and hydrophobic textures for electrically insulating areas. Therefore, the present disclosure provides the following advantages:

The first major advantage of the proposed devices such as mouthguards or healing dressings is the existence of multiple micro-electric fields and micro-electric flows created on the surface of the device on the biological tissues, due to the existence of multiple negative and positive electrodes within the electrical system, accessible to the biological tissues. In this way, instead of a single electric field, as suggested in the prior art, multiple micro-electric fields are created dispersed on the surface of the device, thereby making the stimulation and electric flows on the biological tissues much more efficient and controlled for bone, gum, skin, or other intraoral tissue regeneration and for antibacterial action.

In the proposals already known for dental devices, specifically mouthguards, a single electric field, or a few electric fields, sufficiently spaced apart from each other, with distances greater than 10 mm, are created along the device, which will thus cause a current flow through the tissues in a random and poorly controlled manner, and may therefore be effective where the current passes but poorly effective where the current does not pass, or even excessive if the current flows entirely through a small area and sparse if the current flows through a large volume of fluid.

Alternatively, the present disclosure provides a solution for creating small electric fields along the entire surface of the implant, very close to each other, less than 2 mm apart, making the process of stimulating the surrounding tissues much more effective and controlled across the entire surface of the device. This will have an effect on the effectiveness of the bone and/or soft tissue regeneration process, as well as on antibacterial protection through electrical stimuli, ensuring its effect over the entire surface of the device.

The second major advantage of the proposed device is that distinct surfaces are created, inside and on the outer surface of the device, which promote, delimit, and homogenize the micro-electric flows. A hydrophilic surface with micro-pillars, which ensures the presence of a controlled volume of electrically conductive fluid, and where the micro-electric flows act, and a hydrophobic surface, which repels fluids and is electrically insulating, where electrical stimuli are not intended to exist. This allows the electric flows on the hydrophilic surface to be homogenized and, through the hydrophobic surfaces that delimit the hydrophilic surfaces, prevents electrical losses from the hydrophilic zones to the hydrophobic zones and prevents electric flows in the hydrophobic zones.

The third major advantage of the device is that the existence of distinct zones with different types of surfaces, hydrophilic and/or hydrophobic, allows different electric flows to exist in different zones, isolated from each other, and thus simultaneously perform different types of stimuli, acting differently in different zones, for example eliminating bacteria on the teeth and stimulating gum regeneration. For best results, the device comprises a hydrophobic zone that is non-conductive and does not contain moisture, and a hydrophilic zone comprising pillars for fluid entry, this hydrophilic zone being conductive and containing moisture. The conductive fluid enters through the pillars, passes through the micro-channels, and comes into contact with the electrical system.

The fourth major advantage of the proposed device is that the electrical network can be powered, in addition to the battery, by the forces acting on the devices due to body movements, where a small ball or cylinder, such as a patella, slides inside the piezoelectric element, causing impacts on it, thus generating electric fields which, when acting on the piezoelectric material region, cause the electric field to flow through the circuit of electrical wires inside the device to multiple points on the surface of the device. The action on the piezoelectric material regions and the resulting stimulation of biological tissues is thus achieved in a natural and continuous manner, without the need to assemble batteries or any other device for accumulating electrical potential, either inside or outside the body.

Unlike existing solutions, this solution thus allows action during the desired period of operation for the device, mimicking the piezoelectric effect of collagen contained in bones, gums, skin, and tongue, and making this device solution closer to the natural functioning of natural biological tissues.

Another advantage of the present disclosure is that it is more efficient compared to the prior art as it generates uniform electric current flows by creating multiple micro-electric fields located in the desired areas of the mouthpiece device and at the desired values, preventing the stimuli from deviating to unwanted areas.

In an embodiment, the device comprises a main body based on a polymer selected from polyether ether ketone, silicone, polyethylene terephthalate (PET), polyethylene terephthalate glycol-modified (PETG), polycarbonate, acrylic (polymethyl methacrylate-PMMA), combinations thereof, or composites of the foregoing materials, derivatives thereof, or mixtures thereof—or other materials, all of which are biocompatible and electrically nonconductive.

In an embodiment, the device comprises, on the inner surface of the main body, an electrical circuit, equivalent to the nervous system of a biological body, composed of platinum, rhodium, palladium, silver, gold, alloys of these materials or other biocompatible and electrically conductive material. The system has the ability to transmit micro-electric fields from the electric field generator up to the surface of the mouthpiece device through micro-channels that connect the electrical system and the exterior of the device, where an electrically conductive gel or fluid is located in contact with biological tissues, gums, tooth, or skin, and thus create micro-flows of electric current in the adjacent fluid or gel that will electrically stimulate the tissues adjacent to the mouthpiece device, promoting the regeneration of bone, gums, and skin, and the elimination of bacteria from the same micro-electric fields.

In an embodiment and for best results, the electrical system is powered by a battery, and an electronic control system programmed to operate and create micro-electric fields along the electrical circuit, either in value (Volts), or in operating frequency (Hz), or even in the type of voltage, direct or alternating, or even in the duration of action (seconds), giving rise to micro-electric flows in the adjacent fluids and tissues.

In an embodiment, the electrical system is powered by a piezoelectric component, replacing the battery, assisted by a patella, which slides inside the piezoelectric component, against its walls, due to the movement of the body, thus creating micro-electric fields. This piezoelectric component is made of piezoelectric material selected from $BaTiO_3$ (barium titanate) or other materials with a composition equal or similar to 'perovskite niobate', composed of potassium (K), sodium (Na) and niobium oxide ($NbO_3$) and designated KNN, both of which are biocompatible materials that generate micro-electric fields. The patella is selected from stainless steel, zirconia, alumina, titanium, cobalt-chromium (CoCr) or other metallic or ceramic material that is biologically compatible with intraoral devices or in contact with the skin.

The micro-electric fields are carried to the surface of the mouthguard by the electrical system and micro-channels.

Regarding the electrodes of the electrical system and the battery or the piezoelectric component, including the patella, these are perfectly integrated into the body material of the mouthpiece device. The battery and the piezoelectric component and the electrical system are thus responsible for generating and transmitting, respectively, the micro-electric fields to multiple points across the entire surface of the mouthpiece device, the location of these points and the intensity of the electric fields being customized according to the anatomy, the intended function, and the needs of the user.

In an embodiment, the areas of the mouthpiece device where the micro-electric fields are intended to be created have a physical structure characterized by having micro-pillars and interconnected hollow areas between the pillars, promoting a hydrophilic structure capable of retaining and maintaining a controlled volume of electrically conductive liquid or gel inside, which ensures the occurrence of a controlled electric current flow, and, in the areas where no electric current is intended to exist, the material is hydrophobic, with no space to accommodate liquid or gel, thus preventing electric current flows in these areas, so that the devices thus have areas of their surface where conditions for the existence of controlled electric flows are guaranteed, and other areas of their surface that are electrically insulating, thus ensuring that electric current flows do not flow to undesirable areas, remaining only in the areas where electric current flows are intended to be created, thus ensuring the existence of perfectly defined areas where electric current will flow and areas where electric current will not flow.

In an embodiment, the devices described are obtained using conventional processes such as computer numerical control (CNC) additive printing and micro-machining, in addition to the assembly of wires and electronic devices.

The state of the art relating to mouthpiece devices and mouth healing dressings does not include this type of solution with the creation of multiple micro-electrical stimuli along the body of the devices and with the control of the electric fields, either through the arrangement of the electrical wires or through the specific type of surface to be used. Therefore, the solution now presented offers several innovations and advantages, namely:

- the stimulus for bone and/or gingival and/or dermal regeneration and for antibacterial action is much more efficient and controlled due to the existence of multiple micro-electric fields along the surface of the devices and regions that seek to mimic the piezoelectric regions of biological tissues themselves, generated by a battery and an electronic control system or by a piezoelectric component assisted by a patella, whose electric field is distributed up to the desired surface on each device;
- the stimulus for bone and/or gingival and/or dermal regeneration and for antibacterial action is much more efficient and controlled due to the fact that the devices provide distinct surface areas: a hydrophilic surface area of electrical action, which ensures the existence of a controlled volume of liquid or gel, facilitating and homogenizing the micro-electric flows; and another area with hydrophobic characteristics from which liquids or gel are expelled, thus inhibiting electric flows in these zones and consequently preventing electric flows from diverting to zones where they are not desired. This combination allows control of the location of the micro-electric flows, which are confined to the desired or active zones;
- the electrical system is powered by a battery or, alternatively, by a piezoelectric component, assisted by a patella, which moves inside the piezoelectric element and, through the action of impacts, generates electric fields from the natural forces of chewing or body movement. In both cases, the aim is to have micro-electric fields that mimic the piezoelectric stimuli of the collagen present in the skin, bones, and gums and, therefore, to be stimuli inspired by the biological tissues themselves.

The present disclosure relates to an antimicrobial dental device for tissue regeneration comprising:

- a main body comprising an interior and an exterior surface;
- a plurality of electrodes to stimulate the tissue to regenerate and eliminate bacteria, connected by an electrical circuit; wherein the plurality of electrodes is impregnated throughout the interior of the main body for creating micro-electric fields;
- a plurality of channels, preferably micro-channels, oriented from the outer surface towards the interior of the main body to receive a fluid and direct it to the electrical circuit for creating an electric flow;
- an array of pillars, preferably micro-pillars, which are hydrophilic, wherein the space between each pillar of the pillar array forms a network of capillary channels to receive and retain the electric flow from the plurality of channels near the tissue;
- a hydrophobic and insulating zone inside the main body to repel the electric flow in a zone of the tissue to be protected.

Surprisingly, the device of the present disclosure allows for a significant reduction in the risk of oral infections; the efficient promotion of damaged tissue regeneration and comfort and ease of use, adapting to different users.

In an embodiment for best results, the pillar array is arranged along one part of the interior of the main body and the hydrophobic and insulating region is arranged along another part of the interior of the main body.

In an embodiment for best results, the plurality of channels and the network of capillary channels of the pillar array is a network of interconnected channels.

In an embodiment for best results, the pillar array comprises a plurality of pillars that protrude towards the tissue.

In an embodiment for best results, each pillar of the pillar array has a conical, frustoconical, prismatic, cylindrical or pyramidal shape.

In an embodiment for best results, each of the pillars is at an equidistant distance from the adjacent pillar or pillars.

In an embodiment for best results, each pillar is spaced apart from the adjacent pillar or adjacent pillars by 0.1 to 2 mm.

In an embodiment for best results, each channel of the plurality of channels is arranged equidistant from the adjacent channel or channels.

In an embodiment for best results, each channel is spaced apart from the adjacent channel or channels by 0.5 to 8 mm, preferably 1 to 3 mm.

In an embodiment for best results, the main body is made of polymeric material; preferably the polymer is selected from polyether ether ketone, silicone, polyethylene terephthalate (PET), polyethylene terephthalate glycol-modified (PETG), polycarbonate, acrylic (polymethyl methacrylate-PMMA) or combinations thereof.

In an embodiment for best results, the device of the present disclosure further comprises an electrical system; wherein the electrical system comprises a battery or piezoelectric component.

In an embodiment for best results, the piezoelectric component comprises a patella arranged inside said component for sliding upon movement of the user and creation of the electric field.

In an embodiment for best results, the battery or the piezoelectric component is configured to generate micro-electric fields ranging from 1 mV to 10 V and micro-electric flows ranging from 500 picoamperes to 5 milliamperes.

In an embodiment for best results, the patella is made of a material selected from stainless steel, cobalt-chromium alloy, titanium alloy, zirconia, alumina, or mixtures thereof.

In an embodiment for best results, the electrical system comprises a plurality of electrical wires with positive pole and negative pole, arranged alternately along said device.

In an embodiment for best results, the distances between electrical poles vary from 0.5 to 8 mm, preferably 1 to 3 mm.

In an embodiment for best results, the electrical wires are made of a material selected from gold, silver, platinum, rhodium, palladium, or mixtures thereof.

In an embodiment for best results, the diameter of the wire is from 0.02 to 1 mm.

In an embodiment for best results, the fluid is a liquid selected from saliva, gel.

In an embodiment for best results, the device of the present disclosure may further comprise an active substance, preferably coated or impregnated.

In an embodiment for best results, the active substance is selected from: anti-inflammatory, analgesic, cells, growth factors, or combinations thereof.

In an embodiment for best results, the device is a tray, mouthguard, dressing, or dental bridge.

In an embodiment for best results, the main body has a U-shape configured to be arranged over a plurality of teeth of a user, for partial or total encapsulation of one or more teeth.

In an embodiment for best results, the hydrophobic zone is configured to be positioned over a plurality of the user's teeth.

BRIEF DESCRIPTION OF THE DRAWINGS

For an easier understanding, figures are herein attached, which represent preferred embodiments that are not intended to limit the object of the present description.

DETAILED DESCRIPTION

Figure 1:
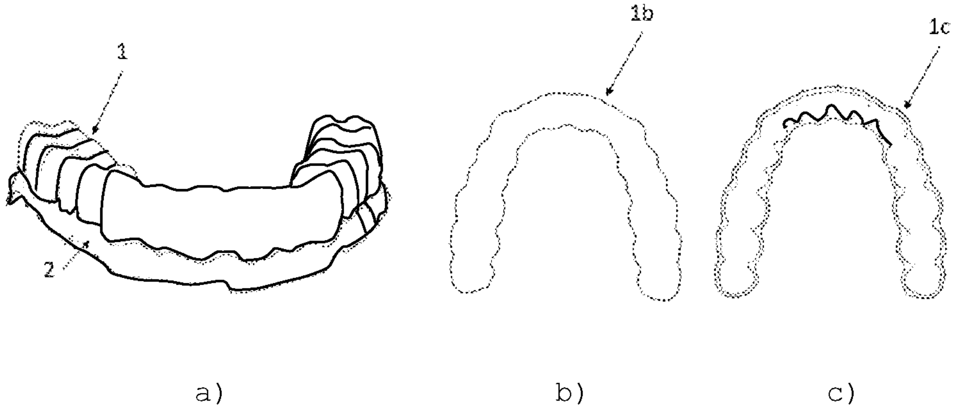
FIG. 1: Schematic representation of an embodiment of a tray-type dental device for antibacterial protection against caries 1, inserted over the teeth, extending to the edge of the gum 2: a) view over the teeth; b) view from above or from the outside 1*b*; c) view from below or from the inside 1*c*.

The present disclosure describes medical devices, more specifically devices for dental use intended for the regeneration of dental, bone, and gingival tissues, and antibacterial action; in particular, an antimicrobial dental device for tissue regeneration comprising:

- a main body comprising an interior and an exterior surface;
- a plurality of electrodes to stimulate the tissue to regenerate and eliminate bacteria, connected by an electrical circuit; wherein the plurality of electrodes is impregnated throughout the interior of the main body for creating micro-electric fields;
- a plurality of channels, preferably micro-channels, oriented from the outer surface towards the interior of the main body to receive a fluid and direct it to the electrical circuit for creating an electric flow;
- an array of pillars, preferably micro-pillars, which are hydrophilic, wherein the space between each pillar of the pillar array forms a network of capillary channels to receive and retain the electric flow from the plurality of channels near the tissue;
- a hydrophobic and insulating zone inside the main body to repel the electric flow in a zone of the tissue to be protected.

The present disclosure relates to a device such as a mouthguard, dental bridge, or healing dressing, a tray capable of stimulating hard tissues such as bone, or soft tissues such as gums or skin, or still eliminating bacteria present in the mouth, teeth, or skin. The stimulation of hard tissues serves to prevent bone recession around implants or even promote its growth if recession has already occurred, and to promote bone regeneration or apposition during orthodontic movement on the side subject to traction, accelerating orthodontic movement. Stimulation of soft tissues serves to prevent gum recession and promote its growth if recession has already occurred, and to promote the healing of ulcers or other injuries to tissues 16 inside the mouth, or still to promote skin healing and regeneration. The elimination of bacteria applies in the following situations: bacteria that adhere to teeth, thus preventing the formation of colonies and consequent formation of caries; bacteria that adhere to dental implants, preventing the formation of biofilms; bacteria that adhere to dental bridges and form biofilms; bacteria that are present in wounds or ulcers of the mouth or skin, preventing infections.

Tissue stimulation 16 and bacteria elimination are caused by the existence of multiple micro-electric fields, distributed uniformly, with the positive 12 and negative 11 poles close enough to be able to create almost constant micro-flows of electric current 3*c* along the surfaces of action. The intensity, frequency, duration of action, and arrangement of these electric fields depend on the biological entities involved, bone, skin, gums 2, bacteria, and are also customized to the specific needs of each patient, in each specific area of the protector or dressing.

In an embodiment, each device allows differentiated micro-electric fields to be programmed along the component, which can be purposely altered over time, depending on the stage of treatment, through the electronic control system 5.

Each device has zones where electrical stimuli are intended to exist and where the electrical poles that promote the micro-electric fields 3*b* are positioned, which in turn produce micro-electric flows 3*c* directly in the biological entities, and zones where electrical insulation is intended, where no electric flows are intended to exist. These electrically insulating zones, in addition to defining the zones that do not require electrical stimuli, also serve to delimit the electric flows, preventing them from flowing randomly. In this sense, where the electric poles are located, the surface consists of hydrophilic micro-pillars 7, capable of retaining a certain volume of liquid or gel, thus helping to control the electric flows through this volume of material connecting the electric poles and the biological tissues 16. In addition, the hydrophilic surface, where electrical stimuli are intended to occur, has micro-channels 4, which establish an electrical connection between the electrical system 3 and the liquid or gel retained in the hydrophilic zone between the pillars. This liquid or gel will absorb the electric current flows, ensuring their conduction through the biological entities in contact with the liquid or gel, namely bacteria, gums 2, skin, among others.

The mouthpiece device has several versions, each one with specific functions, as well as the healing dressing.

In an embodiment, the present description consists of a mouthguard concept 1, 8, 10, 13, 14, 15 composed of a main body made of polymer, specifically polyetheretherketone-Peek, silicone, polyethylene terephthalate-PET, polyethylene terephthalate glycol-modified—PETG, polycarbonate, acrylic (polymethyl methacrylate-PMMA) or still composites of the above materials, derivatives of both or mixtures thereof—or other materials, all of which are biocompatible and non-electrically conductive materials.

In an embodiment, the polymeric main body, preferably made of biocompatible polymer, comprises an electrical circuit inside it, equivalent to the nervous system of a biological body, with the ability to produce micro-electric fields from the electric field generating region up to the surface of the device and thus electrically stimulate, at multiple points, the tissues adjacent to the device through micro-electric fields 3*b*, and to promote micro-electric flows 3*c* in the tissues, consequently causing the regeneration of tissues 16, bone, gum, skin, or the elimination of bacteria in the same tissues, or both simultaneously or alternately.

In an embodiment, this electrical circuit consists of electrically conductive wires with positive pole 12 and negative pole 11, these wires having diameters of 0.02 mm to 1 mm, which depart from a region generating the electric fields consisting of a battery 6*a* or a piezoelectric component 6 such as, for example, barium titanate ($BaTiO3$) or a material with a composition equal or similar to 'niobate perovskite', composed according to the literature of K, Na and $NbO3$ and designated KNN. The piezoelectric component 6 has an area of between 4 and 20 mm2 and a thickness of between 0.1 and 3 mm.

In an embodiment, the electric fields are generated by the battery or, in the case of the piezoelectric component, by the deformation of the piezoelectric component 6 when it is acted upon by a force external to the device, by the deformation caused by the impact of the patella 6*b*, with dimensions of 0.5 to 3 mm in diameter, preferably 1 to 2 mm in diameter and 0.5 to 3 mm thick, preferably 1 to 2 mm thick, in the case of the patella 6*b* is made of stainless steel, titanium, CoCr alloy, zirconia, alumina, or other biologically compatible material, which is incorporated inside the piezoelectric component 6 but can move according to the movement of the body, thus generating impacts on the piezoelectric component 6. The electric fields, with values that can vary from 1 mV to 10 V, flow through the electrical circuit and reach the surface of the implant through micro-channels 4 that connect the electrical circuit to the inner surface of the device in multiple areas which are in contact with the tissues 16, skin, teeth, gums 2, tongue, or other intraoral tissues. The electrical system 3 is responsible for transmitting the micro-electric fields 3*b* from the electric field generating region to the multiple points on the surface of the device.

In an embodiment, the micro-electric fields 3*b* may result from the existence of an electrical system 3 inside the body of the device, which is intended to deliver the micro-electric fields 3*b* generated by a piezoelectric component 6, or by a battery 6*a*, to multiple points on the internal surface of the device, and whose connection between the electrical circuit and the internal zone of the device is made via micro-channels 4, spaced apart from each other by 1 to 3 mm.

The location and intensity of the micro-electric fields 3*b* are defined for each user, taking into account their anatomy and needs, as well as the area and biological entity concerned, but can vary from 1 mV to 10 V, preferably 1 mV to 1 V, and the micro-electric flows 3*c* created can vary from 500 picoamperes to 500 milliamperes, preferably from 500 picoamperes to 5 milliamperes, for distances between electrical poles ranging from 0.5 to 8 mm, preferably 1 to 3 mm.

In an embodiment, the biocompatible polymer main body contains different zones with two different types of surfaces, in the inner zone of the devices, or more precisely in the region of contact with the biological tissues 16.

The surfaces are divided into electrically conductive surfaces and electrically insulating surfaces.

In an embodiment, the electrically conductive surfaces have micro-pillars with a trapezoidal, polygonal, quadrangular, or circular cross-section, whose dimensions vary from 0.1 mm to 0.5 mm at the top of the pillar and 0.15 to 0.8 mm at the base of the pillar, either side or diameter, the height of the pillars varies between 0.1 mm to 2 mm, and the distance between the pillars varies from 0.1 to 2 mm, thus providing hydrophilic characteristics to the pillar structure.

In an embodiment, between the pillars of the hydrophilic structure, there should be bodily fluids, such as saliva, or other non-bodily fluids such as water, or even some gel commonly used in the mouth or on the skin, which ensures that the spaces between the pillars and between the devices and the biological tissues 16 are filled, thus ensuring continuity of electric flows in the hydrophilic surface areas.

In an embodiment, the electrically insulating surfaces are smooth, having no texture, thus preventing the accumulation of any liquid or gel between the devices 1, 8, 10, 13, 14, 15 and the biological tissues 16, teeth, gums, tongue, skin, or other intraoral tissues, thereby preventing or minimizing loss of electric flows to these areas.

FIG. 1 shows an embodiment of the device, wherein the U-shaped device is configured to be arranged over a plurality of teeth of a user. FIG. 1: Schematic representation of an embodiment of a tray-type mouthpiece device for antibacterial protection against caries 1, inserted over the teeth, extending to the edge of the gums 2: a) view over the teeth; b) view from above or from the outside 1*b*; c) view from below or from the inside 1*c*.

Figure 2:
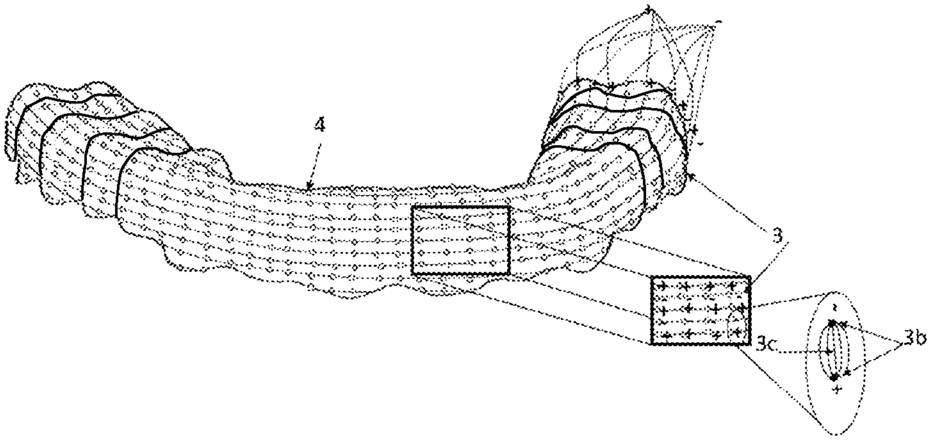
FIG. 2: Schematic representation of a tray-type dental device wherein: a) exterior view with impregnated electrical system 3 and micro-channels 4 between the electrical system and the interior of the tray 4, with micro-electric fields 3*b* and micro-electric flows 3*c*; b) cross-sectional and perspective view of the electrical system 3 and the micro-electric fields and electrical system and micro-channels 4 between the electrical system and the interior of the tray; c) cross-sectional view with detail of the battery 6*a* and electronic control system 5, or piezoelectric component 6 assisted by patella 6*b*.
Figure 2:
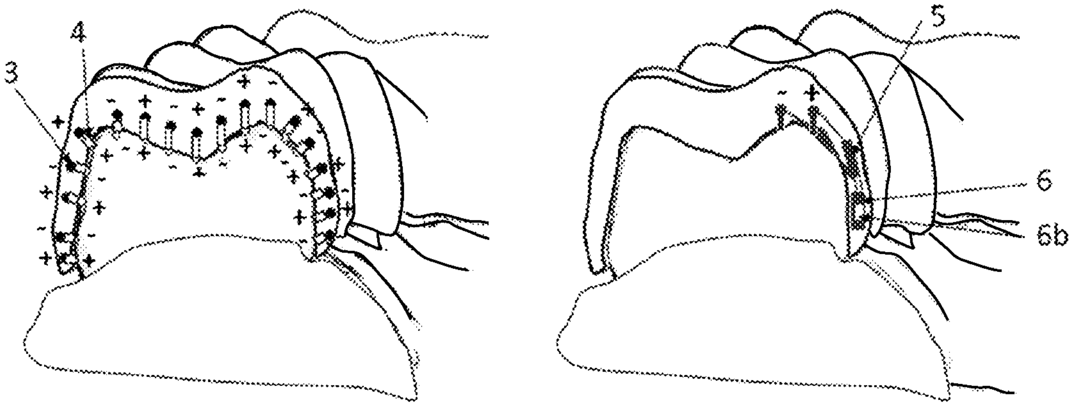

FIG. 2 shows a tray-type dental device. FIG. 2*a*) shows the impregnated electrical system 3 and micro-channels 4 between the electrical system and the interior of the tray 4, with micro-electric fields 3*b* and micro-electric flows 3*c*. FIG. 2*b*) shows the electrical system 3 and the micro-electric fields and electrical system and micro-channels 4 between the electrical system and the interior of the tray. FIG. 2*c*) shows a detail of the battery 6*a* and electronic control system 5, or piezoelectric component 6 assisted by patella 6*b*, a detail of the piezoelectric component 6*b*.

Figure 3:
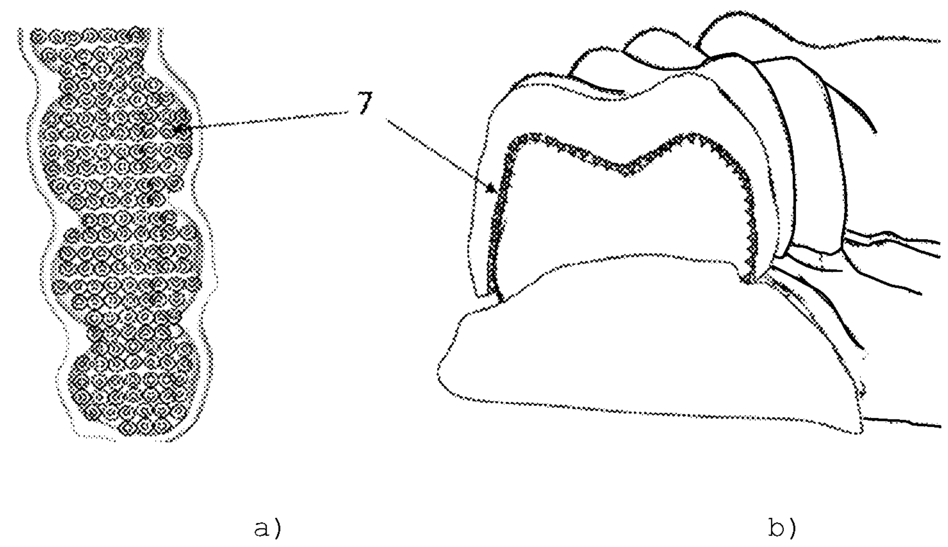
FIG. 3: Schematic representation of a tray-type dental device: a) view of the interior and top of the surface with micro-pillars 7; b) cross-sectional view of the surface with micro-pillars 7.

FIG. 3 shows an embodiment of a tray-type dental device, namely the micro-pillars 7.

Figure 4:
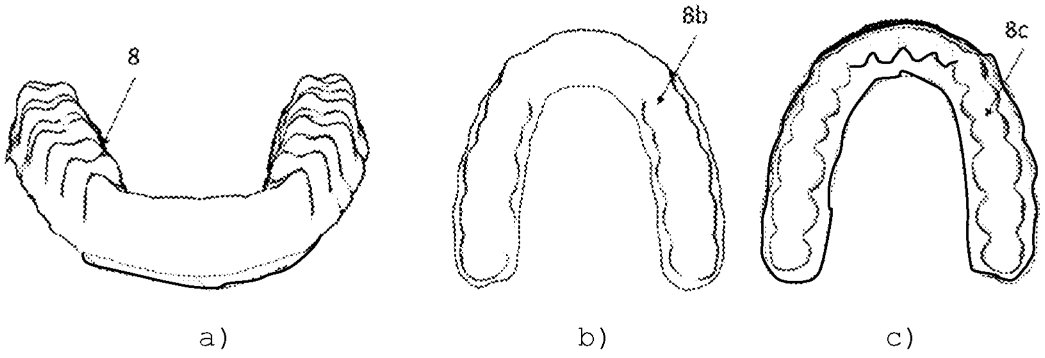
FIG. 4: Schematic representation of an embodiment of the tray-type dental device for gum protection-gingival recession 8: a) view over the teeth and over the gums; b) top view 8*b*; c) bottom view 8*c*.

FIG. 4 shows an embodiment of the tray-type dental device for gum protection-gingival recession 8.

Figure 5:
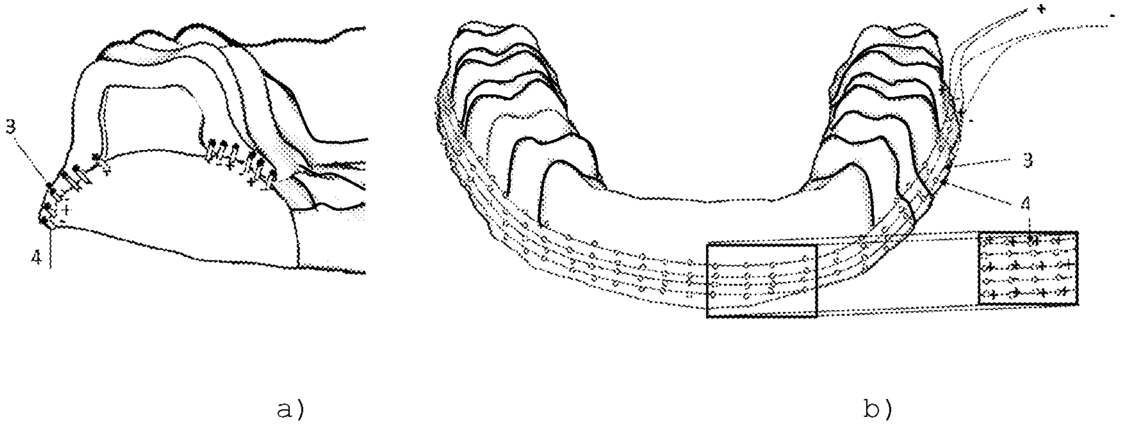
FIG. 5: Schematic representation of an embodiment of the tray-type dental device for gum protection-gum recession 8: a) cross-sectional and perspective view of the impregnated electrical system 3 and the micro-electric fields and micro-channels 4; b) front view of the impregnated electrical system 3 and detail of the micro-electric fields.

FIG. 5 shows an embodiment of the tray-type dental device for gum protection-gingival recession 8, showing the impregnated electrical system 3 and the micro-electric fields and micro-channels 4.

Figure 6:
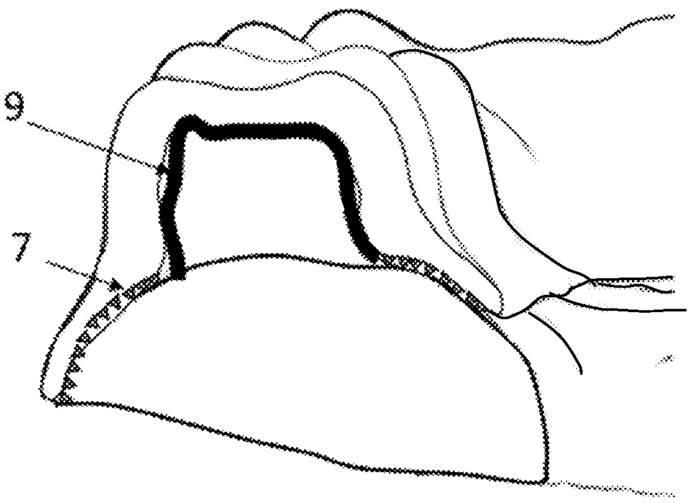
FIG. 6: Schematic representation of a cross-sectional view of an embodiment of the tray-type dental device for protection of the gums-gingival recession 8 with a hydrophilic surface with micro-pillars 7, where the micro-electric fields are intended to act, and a hydrophobic surface 9, where no electric flow is intended to exist.

FIG. 6 shows an embodiment of the tray-type dental device for gum protection-gingival recession 8 with a hydrophilic surface with micro-pillars 7, where the micro-electric fields are intended to act, and a hydrophobic surface 9, where no electric flow is intended to exist.

Figure 7:
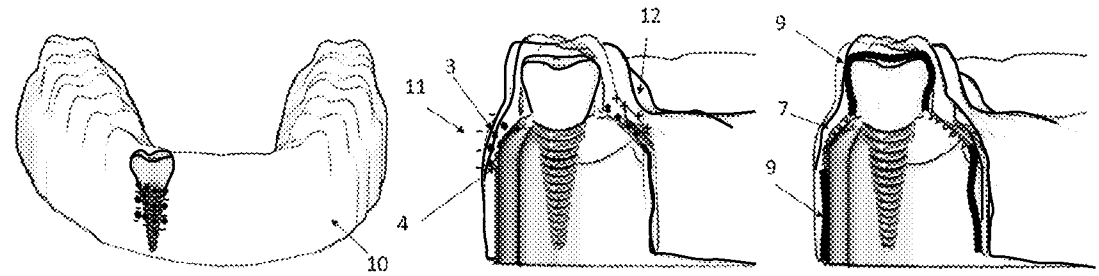
FIG. 7: Schematic representation of an embodiment of the tray-type dental device against biofilm and bone recession 10, around implants: a) exterior view with impregnated electrical system 3, with micro-electric fields 3*b*, in the implant area; b) cross-sectional and perspective view of the electrical system 3, with negative poles 11 and positive poles 12, and of the micro-electric fields 3*b* and electrical system 3, including micro-channels 4 between the electrical system and the interior of the tray in the area around the implant; c) cross-sectional view with detail of the hydrophilic surface with micro-pillars 7, in the area where micro-electric flows are desired, and hydrophobic surface 9 in the area where micro-electric flows are not desired.

FIG. 7 shows an embodiment of the tray-type dental device against biofilm and bone recession 10, around implants, the impregnated electrical system 3, with micro-electric fields 3*b*, in the implant zone; the electrical system 3, with negative poles 11 and positive poles 12, and the micro-electric fields 3*b* and electrical system 3, including micro-channels 4 between the electrical system and the interior of the tray in the area around the implant; the hydrophilic surface with micro-pillars 7, in the area where micro-electric flows are desired, and the hydrophobic surface 9 in the area where micro-electric flows are not desired.

Figure 8:
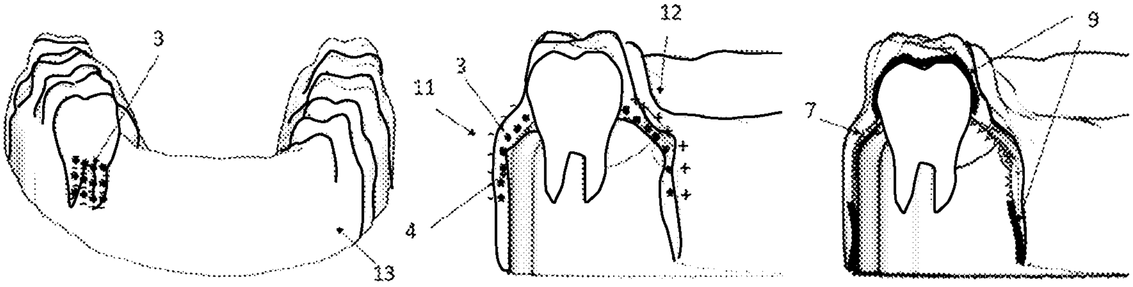
FIG. 8: Schematic representation of an embodiment of the tray-type dental device for accelerating orthodontic movement 13, around the teeth to be moved: a) exterior view with impregnated electrical system, with micro-electric fields 3*b*, with negative poles 11 and positive poles 12, in the area of the teeth to be moved; b) cross-sectional and perspective view of the electrical system 3 and the micro-electric fields 3*b* and electrical system 3, and the micro-channels 4 between the electrical system and the interior of the tray 4 in the area around the teeth to be moved; c) cross-sectional view with detail of the hydrophilic surface 7 with micro-pillars 7, in the area where micro-electric flows are desired, and hydrophobic surface 9 in the area where micro-electric flows are not desired, around the teeth to be moved.

FIG. 8 represents an embodiment of the tray-type dental device for accelerating orthodontic movement 13, around the teeth to be moved, impregnated electrical system, with micro-electric fields 3*b*, with negative poles 11 and positive poles 12, in the area of the teeth to be moved; electrical system 3, and micro-channels 4 between the electrical system and the interior of the tray 4 in the area around the teeth to be moved; and a hydrophilic surface 7 with micro-pillars 7 in the area where micro-electric flows are desired, and a hydrophobic surface 9 in the area where micro-electric flows are not desired, around the teeth to be moved.

Figure 9:
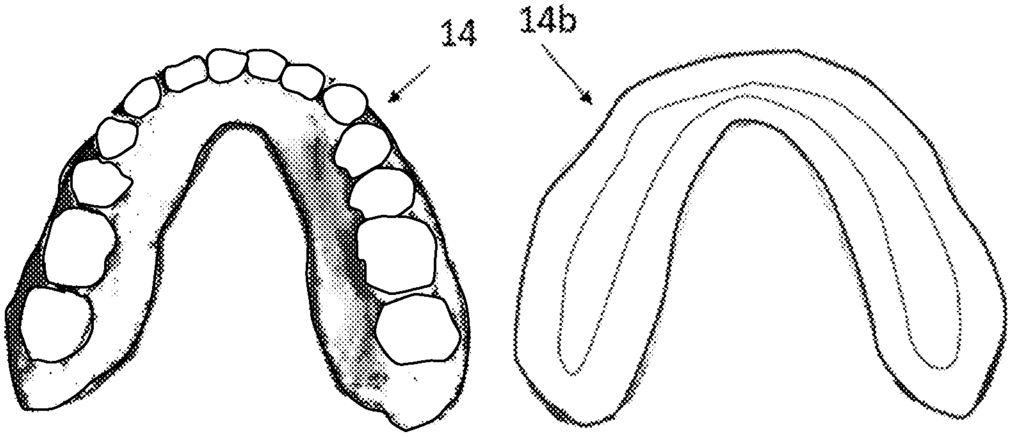
FIG. 9: Schematic representation of an embodiment of the bridge-type dental device with antibacterial protection 14: a) top view 14; b) bottom view 14*b*.

FIG. 9 shows an embodiment of the bridge-type dental device with antibacterial protection 14.

Figure 10:
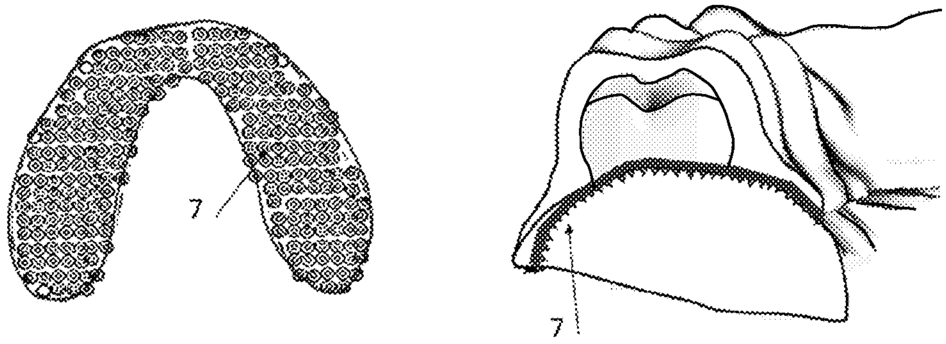
FIG. 10: Schematic representation of an embodiment of the bridge-type dental device with antibacterial protection: a) bottom view showing the physical texture of the hydrophilic surface with micro-pillars (7); b) vertical cross-sectional view showing the physical texture of the hydrophilic surface with micro-pillars (7).

FIG. 10 shows an embodiment of the bridge-type dental device with antibacterial protection: a) bottom view showing the physical texture of the hydrophilic surface with micro-pillars (7); b) vertical cross-sectional view showing the physical texture of the hydrophilic surface with micro-pillars (7).

Figure 11:
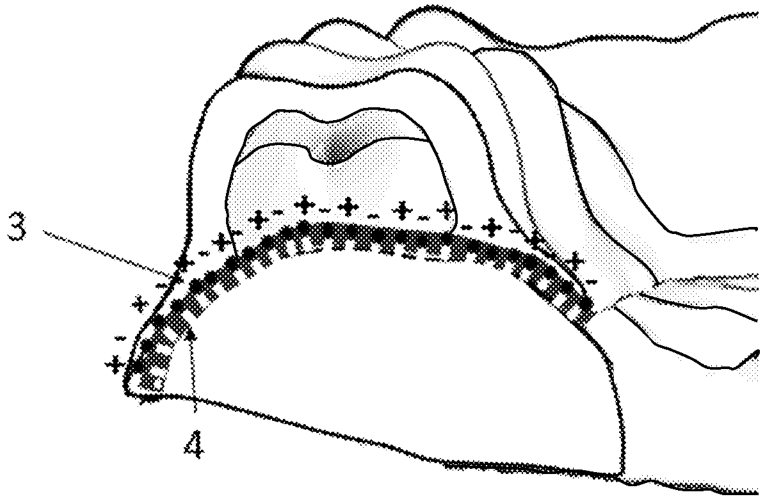
FIG. 11: Schematic representation of an embodiment of the bridge-type dental device with antibacterial protection. Cross-sectional and perspective view of the electrical system impregnated in the dental bridge and the micro-electric fields, and the micro-channels 4 connecting the electrical system 3 and the inner surface of the bridge, in contact with soft tissues.

FIG. 11 shows an embodiment of the bridge-type dental device with antibacterial protection. It shows the electrical system impregnated in the dental bridge and the micro-electric fields 3*b*, and the micro-channels 4 connecting the electrical system (3) and the inner surface of the bridge, in contact with soft tissues.

Figure 12:
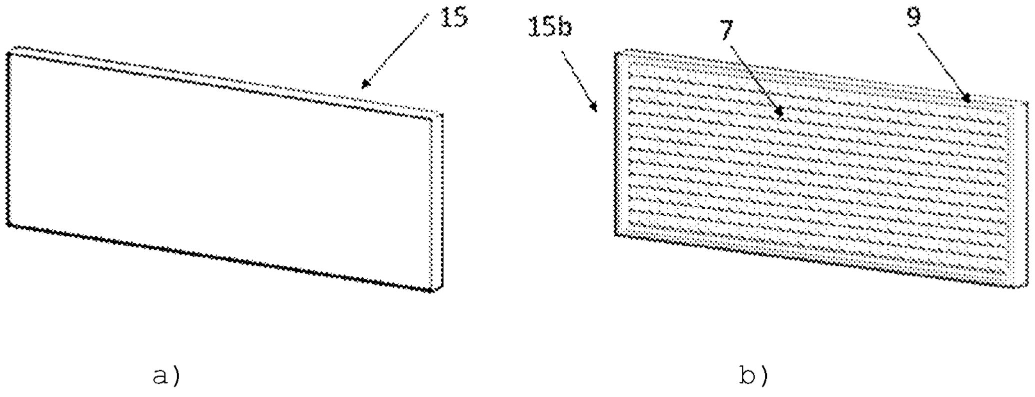
FIG. 12: Schematic representation of an embodiment of the skin-like dental device of the healing dressing type 15: a) top view (15); b) bottom view (15*b*) with detail of the hydrophilic surface with micro-pillars 7, in the area where micro-electric flows are desired, and of the hydrophobic surface 9 in the area where micro-electric flows are not desired.

FIG. 12 shows an embodiment of the skin-like dental device of the healing dressing type 15 with detail of the hydrophilic surface with micro-pillars 7, in the area where micro-electric flows are desired, and of the hydrophobic surface 9 in the area where micro-electric flows are not desired.

Figure 13:
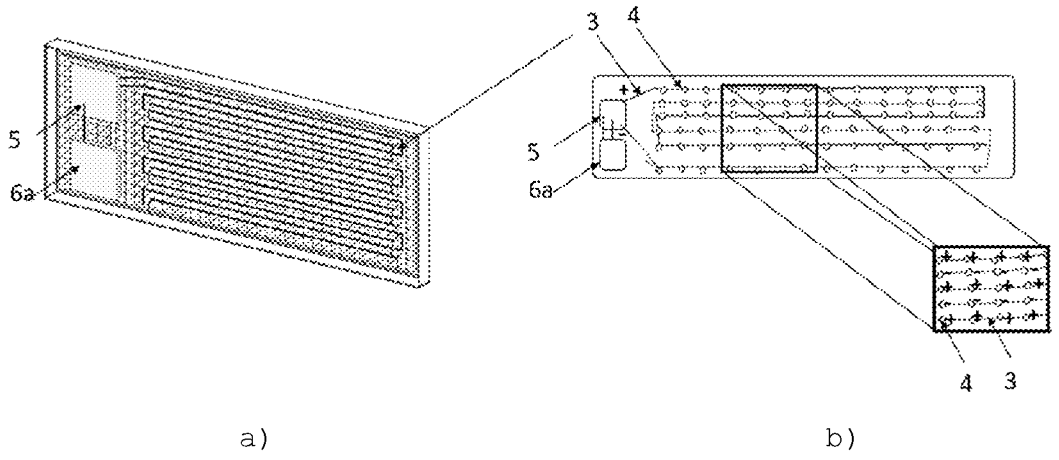
FIG. 13: Schematic representation of an embodiment of the skin-like dental device of the healing dressing type: a) longitudinal cross-sectional view with impregnated electrical system 3, electronic control system 5 and battery 6*a*; b) cross-sectional view of the electrical system 3, micro-channels 4 for contact between the electrical system 3 and the inner surface of the dressing, electronic control system 5 and battery 6*a*.

FIG. 13 shows an embodiment of the skin-like dental device of the healing dressing type with impregnated electrical system 3, electronic control system 5 and battery 6*a*; as well as electrical system 3, micro-channels 4 for contact between the electrical system 3 and the inner surface of the dressing, electronic control system 5 and battery 6*a*.

Figure 14:
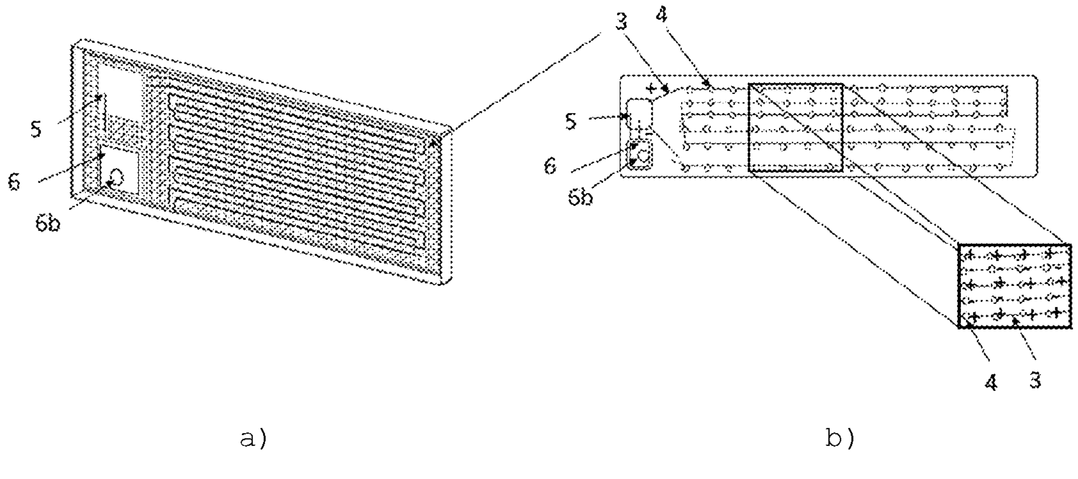
FIG. 14: Schematic representation of an embodiment of the skin-like dental device of the healing dressing type: a) cross-sectional view with impregnated electrical system 3, electronic control system 5 and piezoelectric component 6 with patella 6*b*; b) cross-sectional view of the electrical system 3, micro-channels 4 for contact between the electrical system 3 and the inner surface of the dressing, electronic control system 5 and piezoelectric component 6 with patella 6*b*.

FIG. 14 shows an embodiment of the skin-like dental device of the healing dressing type with impregnated electrical system 3, electronic control system 5, and piezoelectric component 6 with patella 6*b*. FIG. 14 b) shows the electrical system 3, micro-channels 4 connecting the electrical system 3 to the inner surface of the dressing, electronic control system 5 and piezoelectric component 6 with patella 6*b*.

Figure 15:
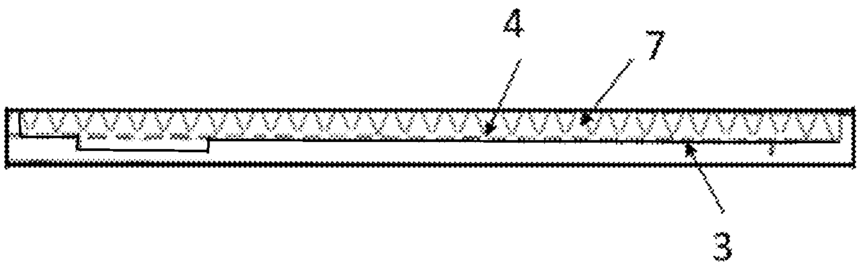
FIG. 15: Schematic representation of an embodiment of the skin-like dental device of the healing dressing type: a) Side cross-sectional view showing the impregnated electrical system 3, the micro-channels 4 connecting the electrical system 3 with the liquid or gel, which is accommodated between the micro-pillars 7.

FIG. 15 shows an embodiment of the skin-like dental device of the healing dressing type, showing the impregnated electrical system 3, the micro-channels 4 connecting the electrical system 3 with the liquid or gel, which is accommodated between the micro-pillars 7.

Figure 16:
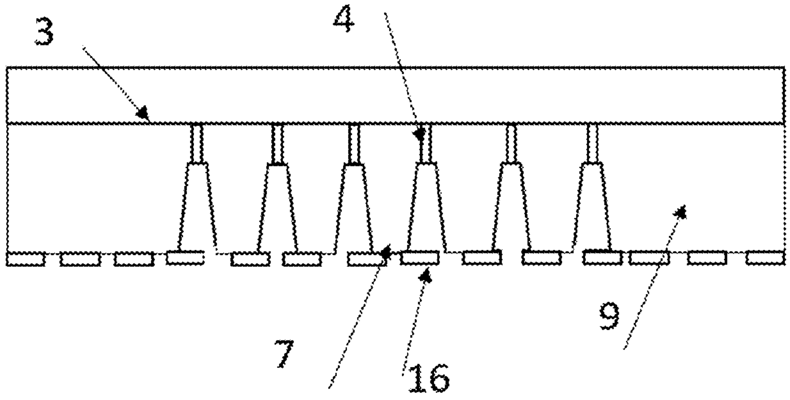
FIG. 16: Schematic representation of an embodiment of the mouthpiece or skin device: Side cross-sectional view showing the impregnated electrical system 3, the micro-channels 4 connecting the electrical system 3 with the liquid or gel, which is accommodated between the micro-pillars 7 in the hydrophilic zone, the hydrophobic zone 9, and the biological tissues 16, tooth, gum, skin, tongue, or other intraoral tissues.

FIG. 16 shows an embodiment of the dental device, showing the impregnated electrical system 3, the micro-channels 4 connecting the electrical system 3 to the liquid or gel, which is accommodated between the micro-pillars 7 in the hydrophilic zone, the hydrophobic zone 9, and the biological tissues 16, tooth, gum, skin, tongue, or other intraoral tissues.

The term "comprises" or "comprising" whenever used in this document is intended to indicate the presence of stated characteristics, elements, integers, steps, and components, but not to preclude the presence or addition of one or more other characteristics, elements, integers, steps, and components, or groups thereof.

The present invention is, of course, in no way restricted to the embodiments described herein, and a person with average skills in the art will be able to foresee many possibilities for modification thereof and for substitution of technical characteristics with equivalent ones, depending on the requirements of each situation, as defined in the appended claims.

The following claims define additional embodiments of the present description.

BIBLIOGRAPHIC REFERENCES

[1] Gonçalves, I. M. R.; Carvalho, O.; Henriques, B.; Teughels, W.; Souza, J. C. M.; Electrical potential approaches to inhibit biofilm adhesion on titanium implants, Materials Letters, 2019, 255, 126577

[2] Bins-Ely, L.; Suzuki, D.; Magini, R.; Henriques, B.; Souza, J. C. M.; Enhancing the bone healing on electrical stimuli through the dental implant, Computer Methods in Biomechanics and Biomedical Engineering, 2020, 23(14), pp. 1041-1051.

[3] Bins-Ely, L. M.; Cordero, E. B.; Souza, J. C. M.; Benfatti, C. A. M.; Magini, R. S.; In vivo electrical application on titanium implants stimulating bone formation, Journal of Periodontal Research, 2017, 52(3), pp. 479-484.

The invention claimed is:

1. An antimicrobial and tissue regenerative dental device comprising:

- a main body comprising an interior and an exterior surface;
- a plurality of electrodes to stimulate the tissue to regenerate and eliminate bacteria, connected by an electrical circuit; wherein the plurality of electrodes is impregnated throughout the interior of the main body for creating micro-electric fields;
- a plurality of channels, oriented from the outer surface towards the interior of the main body to receive a fluid and direct it to the electrical circuit for creating an electric flow;
- an array of hydrophilic pillars, wherein the space between each pillar of the pillar array forms a network of capillary channels to receive and retain the electric flow from the plurality of channels near the tissue;
- a hydrophobic and insulating zone inside the main body to repel the electric flow in a zone of the tissue to be protected.

2. The device according to claim 1, wherein the pillar array is arranged along one part of the interior of the main body and the hydrophobic and insulating region is arranged along another part of the interior of the main body.

3. The device according to claim 1, wherein the plurality of channels and the network of capillary channels of the pillar array is a network of interconnected channels.

4. The device according to claim 1, wherein the pillar array comprises a plurality of pillars that protrude towards the tissue.

5. The device according to claim 1, wherein each pillar of the pillar array has a conical, frustoconical, prismatic, cylindrical or pyramidal shape.

6. The device according to claim 1, wherein each of the pillars is at an equidistant distance from the adjacent pillar or pillars.

7. The device according to claim 1, wherein each pillar is spaced apart from the adjacent pillar or adjacent pillars by 0.1 to 2 mm.

8. The device according to claim 1, wherein each channel of the plurality of channels is arranged equidistant from the adjacent channel or channels.

9. The device according to claim 1, wherein each channel is spaced apart from the adjacent channel or channels by 0.5 to 8 mm.

10. The device according to claim 1, wherein the main body is made of polymeric material.

11. The device according to claim 1, further comprising an electrical system, wherein the electrical system comprises a battery or piezoelectric component.

12. The device according to claim 1, wherein the electrical system comprises a plurality of electrical wires with positive pole and negative pole, arranged alternately along said device.

13. The device according to claim 1, wherein the fluid is a liquid selected from saliva, gel.

14. The device according to claim 1, wherein the device further comprises an active substance.

15. The device according to claim 1, wherein the device is a tray, mouthguard, dressing, or dental bridge.

16. The device according to claim 1, wherein the main body has a U-shape configured to be arranged over a plurality of teeth of a user, for partial or total encapsulation of one or more teeth.

17. The device according to claim 1, wherein the plurality of channels are micro-channels.

18. The device according to claim 1, wherein the hydrophilic pillars are micro-pillars.

19. The device according to claim 9, wherein each channel is spaced apart from the adjacent channel or channels by 1 to 3 mm.

* * * * *